(12) United States Patent
Moghe et al.

(10) Patent No.: US 8,929,507 B2
(45) Date of Patent: Jan. 6, 2015

(54) METHOD AND SYSTEM FOR SUBSTANTIALLY REDUCING RING ARTIFACT BASED UPON RING STATISTICS

(75) Inventors: Sachin Moghe, Northbrook, IL (US); Michael D. Silver, Northbrook, IL (US)

(73) Assignees: Kabushiki Kaisha Toshiba, Tokyo (JP); Toshiba Medical Systems Corporation, Tochigi-Ken (JP)

( * ) Notice: Subject to any disclaimer, the term of this patent is extended or adjusted under 35 U.S.C. 154(b) by 0 days.

(21) Appl. No.: 13/276,551

(22) Filed: Oct. 19, 2011

(65) Prior Publication Data

US 2013/0101080 A1    Apr. 25, 2013

(51) Int. Cl.
| A61B 6/03 | (2006.01) |
| G01N 23/04 | (2006.01) |
| G06T 11/00 | (2006.01) |
| A61B 6/00 | (2006.01) |

(52) U.S. Cl.
CPC ............... *A61B 6/03* (2013.01); *G01N 23/046* (2013.01); *G06T 11/005* (2013.01); *A61B 6/032* (2013.01); *A61B 6/4233* (2013.01); *A61B 6/5205* (2013.01); *A61B 6/5258* (2013.01)
USPC ................... 378/4; 378/19; 378/207; 382/131

(58) Field of Classification Search
CPC .... A61B 6/032; A61B 4/5205; A61B 6/5258; G01N 23/046; G06T 11/005
USPC ................... 378/4, 19, 207; 382/131
See application file for complete search history.

(56) References Cited

U.S. PATENT DOCUMENTS

| 4,352,020 | A | * | 9/1982 | Horiba et al. | 378/18 |
|---|---|---|---|---|---|
| 4,654,796 | A | * | 3/1987 | Takagi et al. | 378/10 |
| 5,430,785 | A | * | 7/1995 | Pfoh et al. | 378/19 |
| 5,473,663 | A | * | 12/1995 | Hsieh | 378/207 |
| 5,533,081 | A | * | 7/1996 | Hsieh | 378/15 |
| 5,734,691 | A | * | 3/1998 | Hu et al. | 378/4 |
| 5,841,828 | A | * | 11/1998 | Gordon et al. | 378/4 |
| 6,148,057 | A | * | 11/2000 | Urchuk et al. | 378/18 |
| 6,819,734 | B2 | * | 11/2004 | Raupach | 378/4 |
| 7,056,018 | B2 | * | 6/2006 | Stierstorfer et al. | 378/207 |
| 7,391,927 | B2 | * | 6/2008 | Stierstorfer | 382/275 |
| 7,656,990 | B2 | * | 2/2010 | Wigstrom et al. | 378/4 |
| 7,676,073 | B2 | * | 3/2010 | Hamill et al. | 382/128 |
| 8,218,715 | B2 | * | 7/2012 | Sauer et al. | 378/4 |
| 8,520,974 | B2 | * | 8/2013 | Fujita et al. | 382/275 |
| 2003/0103595 | A1 | * | 6/2003 | Raupach | 378/4 |
| 2004/0022364 | A1 | * | 2/2004 | Stierstorfer et al. | 378/207 |
| 2005/0226366 | A1 | * | 10/2005 | Hsieh et al. | 378/16 |
| 2011/0007956 | A1 | * | 1/2011 | Meyer et al. | 382/131 |

* cited by examiner

*Primary Examiner* — Allen C. Ho
(74) *Attorney, Agent, or Firm* — Yoshida & Associates, LLC (57) ABSTRACT

The current invention is generally related to an image processing method and system for substantially reducing ring artifacts. Using the attenuation data, the ring artifacts are substantially prevented based upon two-step process, and the second ring artifact reduction step removes the undesirable rings based upon previously determined statistical data including mean and standard deviation.

12 Claims, 7 Drawing Sheets

NO RING CORRECTION

FIG. 9B

STANDARD v11.7 sRFC

SE2  SE1  SE3  SE4
WINDOW LEVEL/WIDTH: −235/500

FIG. 9C

PROPOSED sRFC

FIG. 10A

NO RING CORRECTION

FIG. 10B

STANDARD v11.7 sRFC

SE  Brd

FIG. 10C

PROPOSED sRFC

Brd

FIG. 11A  
NO RING CORRECTION

FIG. 11B  
STANDARD v11.7 sRFC

Brd  
WINDOW LEVEL/WIDTH: 200/750

FIG. 11C  
PROPOSED sRFC

US 8,929,507 B2

METHOD AND SYSTEM FOR SUBSTANTIALLY REDUCING RING ARTIFACT BASED UPON RING STATISTICS

FIELD OF THE INVENTION

The current invention is generally related to a ring artifact reduction method and system utilizing ring statistics.

BACKGROUND OF THE INVENTION

Ring artifacts also known as simply rings are a persistent problem in almost all commercially sold CT-scanners when the source and detector rotate as a unit around the object under examination or the source and detector are alternatively fixed and the object rotates on a turntable. This is called rotate-rotate geometry, also known as third generation geometry. The ring artifacts are associated with various medical scanners such as diagnostic head and body scanners based on a torus-design as well as interventional scanners and on-board scanners on radiotherapy machines based on C-arm design. Furthermore, the ring artifacts affect many industrial CT-scanners.

It appears that rings arise in CT-images from nonlinearities among the different sensors in the detector. For example, consider all detector elements of the detector to be perfectly balanced with the same response for the same input signal except for one element. Because of the nature of the rotate-rotate geometry, any detector element including the unbalanced detector element records the transmission ray paths tangent to a circle of fixed radius. The radius of the artifact is determined by how far the unbalance element is from the column of elements that nearly coincide with the projection of the rotation axis of the scanner. Consequently, during the backprojection step in the reconstruction process, the anomalies along these tangent ray paths constructively build up to form a ring or arc in the image.

Rather than eliminating the nonlinearities in the detector elements, prior art has attempted to remove the ring artifacts in the data or images. Prior art has attempted three basic approaches to remove ring artifacts including calibration, filtering out ring-causing components in the data (sinogram) domain and filtering out the rings in the image domain. Although many prior art CT-systems appear to use all three approaches, the details of ring artifact removal algorithms are closely held trade secrets amongst the commercial manufacturers. In any case, in spite of the above prior art techniques, a practical solution is still desired for a method and a system for substantially reducing ring artifacts.

DETAILED DESCRIPTION OF THE PREFERRED EMBODIMENT(S)

In the following, one exemplary embodiment of substantially reducing the ring artifacts is implemented on a multi-slice X-ray computer tomography (CT) scanner according to the current invention. Despite the specific exemplary implementation, the currently claimed invention is not limited to a particular implementation based upon the X-ray CT scanner. In general, the currently claimed invention is applicable to other types of scanners such as C-arm design scanners that include arrays of detector elements.

In general, a combination of hardware and software performs the tasks or steps involved in a process of substantially reducing the ring artifacts according to the current invention. In the following description, unless it is specifically disclosed, embodiments are meant to utilize any combination of hardware and software to implement the tasks or steps involved in a process of substantially reducing the ring artifacts. In one embodiment, relevant software, modules are provided to an existing multi-slice X-ray computer tomography (CT) scanner to perform the tasks of substantially reducing the ring artifacts according to the current invention.

Figure 1:
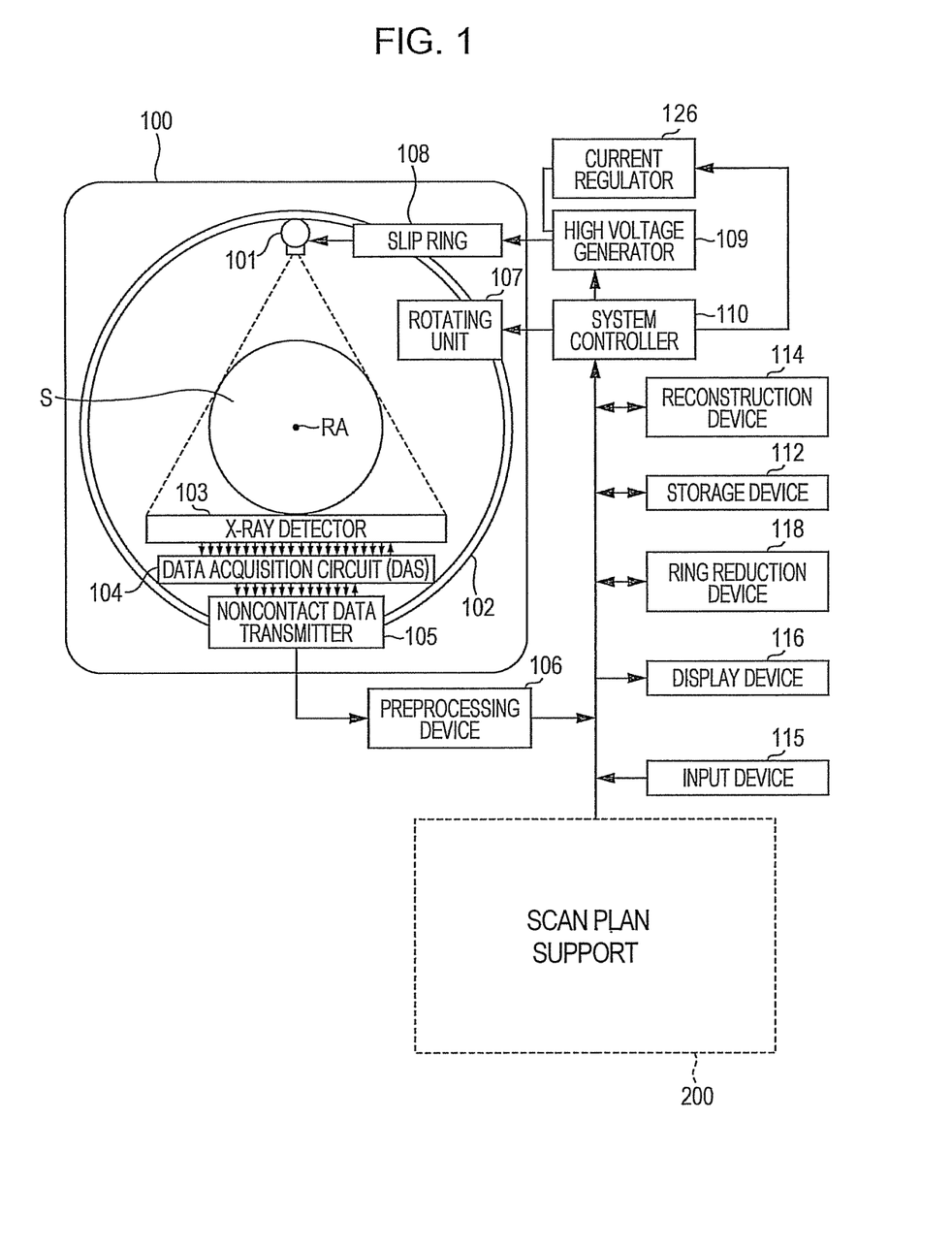
FIG. 1 is a diagram illustrates one embodiment of the multi-slice X-ray CT apparatus or scanner according to the current invention.

Referring now to the drawings, wherein like reference numerals designate corresponding structures throughout the views, and referring in particular to FIG. 1, a diagram illustrates one embodiment of the multi-slice X-ray CT apparatus or scanner according to the current invention including a gantry 100 and other devices or units. The gantry 100 is illustrated from a front view and further includes an X-ray tube 101, an annular frame 102 and a multi-row or two-dimensional array type X-ray detector 103. The X-ray tube 101 and X-ray detector 103 are diametrically mounted across a subject S on the annular frame 102, which rotates around an axis RA. A rotating unit 107 rotates the annular frame 102 at a high speed such as 0.4 sec/rotation while the subject S is being moved along the axis RA into or out of the illustrated page.

The multi-slice X-ray CT apparatus further includes a current regulator 126, a high voltage generator 109 that applies a tube voltage to the X-ray tube 101 via slip ring 108 so that the X-ray tube 101 generates X ray. In one embodiment, the high voltage generator 109 is mounted on the annular frame 102. The X rays are emitted towards the subject S, whose cross sectional area is represented by a circle. The X-ray detector 103 is located at an opposite side from the X-ray tube 101 across the subject S for detecting the emitted X rays, some of which have attenuated by transmitting through the subject S. Thus, the detected X rays are also attenuated data or signals.

Still referring to FIG. 1, the X-ray CT apparatus or scanner further includes other devices for processing the detected signals from X-ray detector 103. A data acquisition circuit or a Data Acquisition System (DAS) 104 converts a signal output from the X-ray detector 103 for each channel into a voltage signal, amplifies it, and further converts it into a digital signal. The X-ray detector 103 and the DAS 104 are configured to handle a predetermined total number of projections per rotation (TPPR).

The above described data is sent to a preprocessing device 106, which is housed in a console outside the gantry 100 through a non-contact data transmitter 105. The preprocessing device 106 performs certain corrections such as sensitivity correction on the raw data. Furthermore, the preprocessing device 106 optionally generates the attenuation log data from the attenuation data. A storage device 112 then stores the resultant data that is also called projection data at a stage immediately before reconstruction processing. The storage device 112 is connected to a system controller 110 through a data/control bus, together with a reconstruction device 114, display device 116, input device 115, a ring reduction device 118 and the scan plan support apparatus 200. The scan plan support apparatus 200 includes a function for supporting an imaging technician to develop a scan plan.

The reconstruction device 114 optionally reconstructs the image based upon the preprocessed data stored in the storage device 112. During backprojection operation of the reconstruction process also known as the backprojection step, the anomalies along these tangent ray paths constructively build up to form a ring or arc as the image is reconstructed, and these undesirable rings in the reconstructed image are called ring artifacts. It is speculated that the anomalies are caused by many possible sources that are related to nonlinearities among the sensors in the detector.

Figure 2:
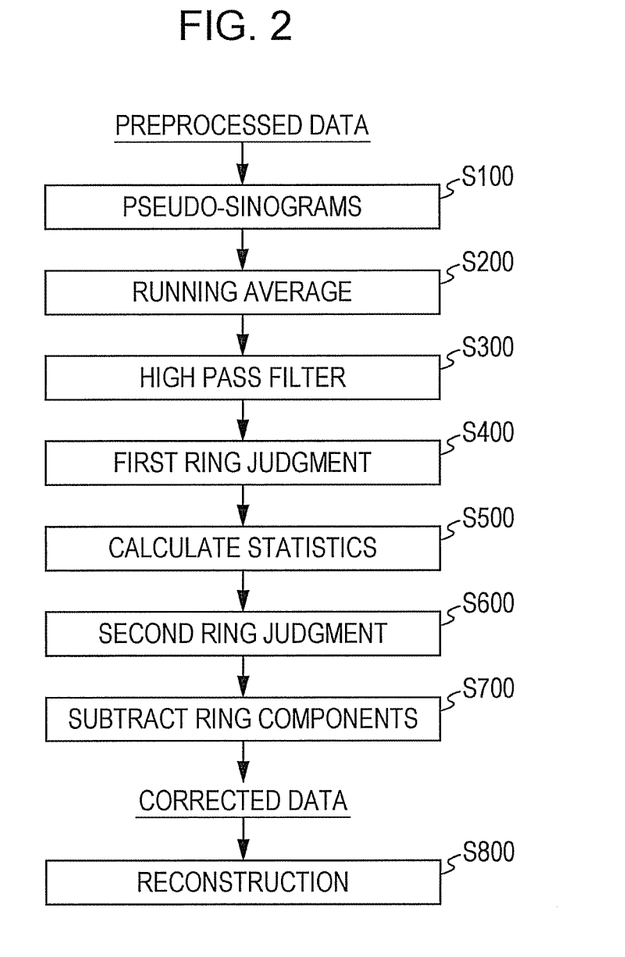
FIG. 2 is a flow chart illustrating steps or tasks involved in an exemplary process of substantially reducing the ring artifacts according to the current invention.

FIG. 2 is a flow chart illustrating steps or tasks involved in an exemplary process of substantially reducing the ring artifacts according to the current invention. In one embodiment of the current invention, sinogram-based ring free correction (sRFC) is applied to the preprocessed data, and sRFC includes at least five steps. sRFC smoothes pseudo-sinograms along the frame direction to remove certain high-frequency structure. In this regard, a prior art judgment function including a high pass filter along the column removes the consistent anomalies from column to column in the data. Unfortunately, the prior art judgment function alone tends to cause unintended side effects in which residual structure is confused for a ring component. A predetermined judgment function according to the current invention substantially prevents these side effects.

In various embodiments, sRFC is optionally applied at different points with respect to preprocessing and reconstruction. In one embodiment as illustrated in FIG. 2, sRFC is applied after preprocessing but before reconstruction. In another embodiment, sRFC is applied in the midst of preprocessing, after linearization (flood or equivalent normalization) but before logarithmic conversion.

FIG. 2 illustrates various steps of sRFC that are performed on the preprocessed data. In step S100, if necessary, the processed data is sorted in a predetermined pseudo-sinogram format. After the preprocessed data is sorted in the step S100, the running average is determined over a certain number of frames in step S200 according to a predetermined boundary rule. The step S200 effectively smoothes the pseudo-sinograms. Subsequently, step S300 produces the candidates for the ring components by applying a predetermined high-pass filter to the smoothed pseudo-sinograms from the step S200. A predetermined first judgment function in step S400 is to prevent unintended side effects from the correction based upon a predetermined fuzzy logic to the ring components candidates that have been previously determined in the step S300. The predetermined first judgment function has a relatively coarse determination in preventing the unintended side effects. After the coarse judgment function in the step S400, step S500 calculates its mean and standard deviation for each ring component. The exemplary process of substantially reducing the ring artifacts according to the current invention performs a predetermined second judgment function in step S600 to further suppress unintended side effects from the correction by applying the fuzzy logic to the previously determined ring component candidates. The second judgment function is based upon the mean and standard deviation for each ring component in the step S500. Lastly, the exemplary process in step S700 according to the current invention subtracts the true ring components as determined in the step S600 from the preprocessed data to generate desirably corrected data for reconstruction so that step S800 reconstructs the image based upon the corrected data.

With respect to the above described exemplary process, the preprocessing device 106 and the ring reduction device 118 perform certain tasks or steps in the substantial reduction of the ring artifacts according to the current invention. Furthermore, the ring reduction device 118 includes a first ring judgment unit and a second ring judgment unit for performing some or all of the steps S100 through S700 of FIG. 2. The particular division of these steps and tasks are dependent on a particular implementation of software modules and hardware modules.

Instead of the above described exemplary process of applying sRFC, one alternative embodiment optionally performs an image-based correction (iRFC), which explicitly determines rings and arcs in the reconstructed image. However, iRFC generally has several problems including difficulties in differentiating rings from nearly circular structures and other unintended side effects. For these reasons, another alternative embodiment for substantially reducing the ring artifacts converts the reconstructed image data back into the projection data including sRFC or iRFC before performing the above described steps S100 through S700 in order to generate the desirably corrected data before reconstructing again in step S800.

Figure 3A:
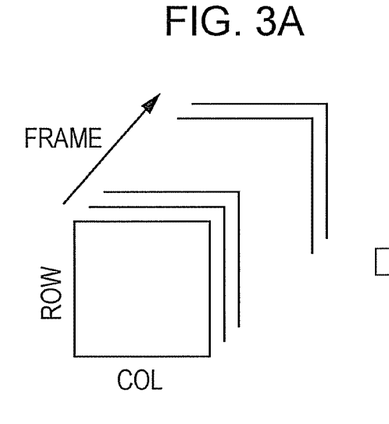
FIG. 3A illustrates that the preprocessed data is sorted in rows by columns for each frame.
Figure 3B:
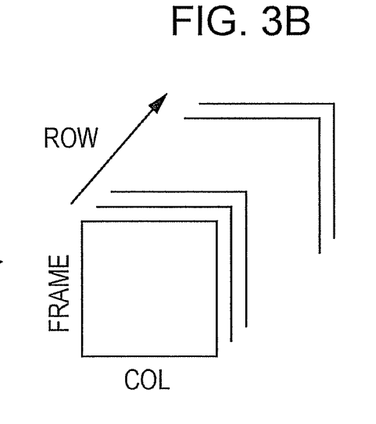
FIG. 3B illustrates that the row-by-column format of FIG. 3A is converted into a predetermined pseudo-sinogram format.

In the following, each of the steps S100 through S700 of the exemplary process will be further described in detail according to the current invention. In the step S100 of one exemplary embodiment of the current invention, the preprocessed data is converted into a predetermined pseudo-sinogram format for the subsequent processing. Now referring to FIG. 3A, assuming that the preprocessed data is sorted in rows by columns for each frame. This row-by-column format is converted into a predetermined pseudo-sinogram format as illustrated in FIG. 3B. As already described, since sRFC processes the data row by row, the preprocessed data is sorted into pseudo-sinograms according to a transpose of two of the three data coordinates.

The acquired data forms a display of columns across as it is viewed vertically if the acquired preprocessed data is sorted in pseudo-sinograms for a given detector row. The acquired data is processed through flood or equivalent normalization, and ring components are consequently observed as vertical streaks. In fact, sinogram-based ring free correction (sRFC) works best if detector anomalies are identified for sensor by sensor so as to make one column-wide vertical streaks in the pseudo-sinograms. sRFC is not particularly effective if several contiguous sensors across the columns of the detector coherently result in the same anomalies. The anomalies over several contiguous sensors across the columns of the detector give rise to circular band artifacts rather than ring artifacts.

In the step S200 of one exemplary embodiment of the current invention, the running average is determined over frames to effectively smooth the pseudo-sinograms. The running average is adaptive: the running average optionally depends on a column index value. The boundary conditions for the running average depend on acquisition mode: full-scan circular, helical, or half-scan circular. For full-scan, the first frame wraps to the last frame and vice-versa. For helical, there needs be no explicit boundary condition except at the very beginning and end of the acquisition, in which case it can use the half-scan boundary condition. For half-scan, the filter length becomes asymmetric for the first and last frames.

Figure 4A:
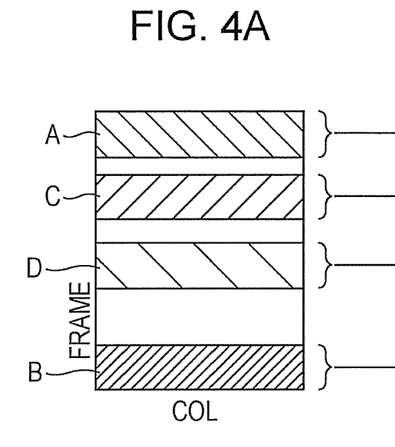
FIG. 4 diagrammatically illustrate the above described running average step.
Figure 4B:
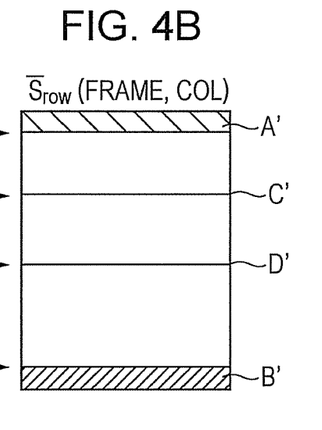

FIG. 4 diagrammatically illustrate the above described running average step. For example, FIG. 4A illustrates that a main loop or regular running average processing performs on portions C and D of the pseudo-sinograms while a sub loop or boundary condition running average processing performs on portions A and B of the pseudo-sinograms. As a result of the above running average processing, FIG. 4B illustrates that the boundary condition the smoothed outputs A' and B' on the right side are the same while the smoothed results C' and D' from the main loop are different. For simplicity, the example assumes the number of frames in the running average processing is the same for all columns.

Figure 5:
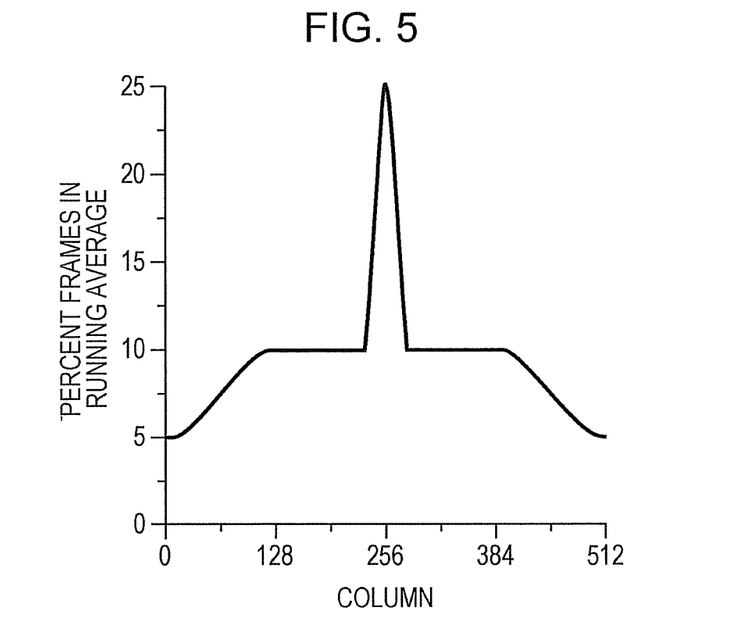
FIG. 5 is an exemplary continuous function, assuming that the most frames in the running average is 25% of the number of frames in the patient data set.

In the step S200 of another exemplary embodiment of the current invention, the running average is determined over varying frames to effectively smooth the pseudo-sinograms. The running average is over a varying number of frames depending upon a particular column, and the number of the frames is also a length of the running average. For example, stronger correction is needed in the center because the energy of the anomaly is wrapped up into a tiny circumference compared with the same anomaly from a sensor near the edge of the detector. FIG. 5 is an exemplary continuous function, assuming that the most frames in the running average is 25% of the number of frames in the patient data set.

In the step S300, the result produces the candidates for the ring components by applying a predetermined high-pass filter to the smoothed pseudo-sinograms from the step S200. The input to the high-pass filter includes the smoothed pseudo-sinogram and a predetermined length M of the median filter in one implementation. Optionally, a linear filter is used in another implementation among other filters. The output from the high-pass filter includes ring component candidate. Certain boundary conditions are predetermined, and such conditions are that for the first M/2 and last M/2 elements are not filtered. The rings components are initialized to zero.

Figure 6:
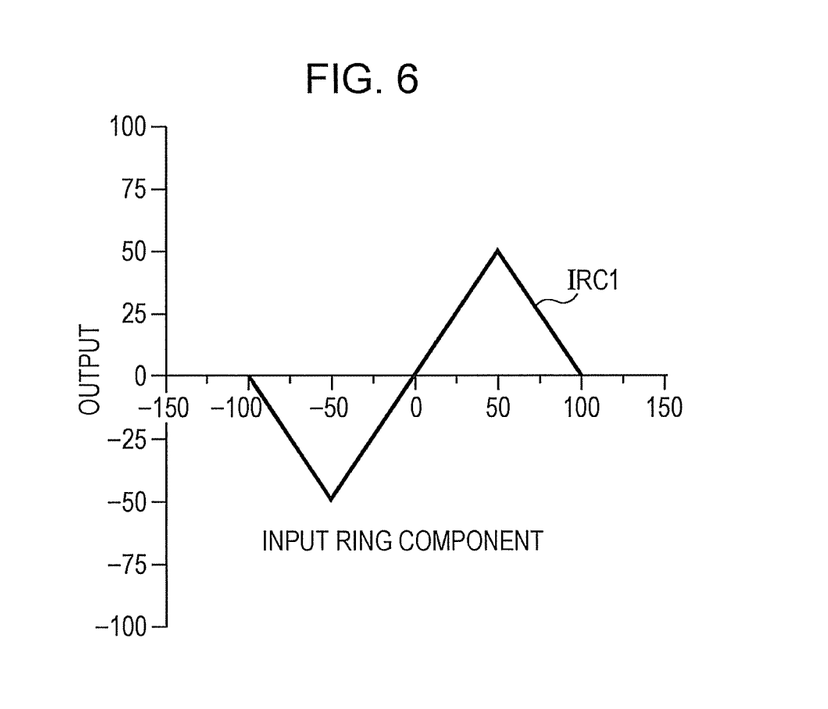
FIG. 6 illustrates one exemplary first ring judgment function IRC 1.

In the step S400, the first ring judgment is to prevent unintended side-effects from the correction by applying fuzzy logic to the ring component candidates from the previously performed high-pass filtered results. For example, the input to the first ring judgment includes the ring component candidates, the output of preprocessing, ring amplitude fraction and minimum ring amplitude while the output is the ring components of the data after the first ring judgment. FIG. 6 illustrates one exemplary first judgment function IRC 1.

Following the step S400, one exemplary embodiment of the current invention generates ring component statistics in the step S500 based upon a predetermined set of rules. For example, the input to determine the statistics includes the ring components of the data after first judgment function while the output statistics includes the mean of the ring components averaged over frames and the standard deviation of the ring components. For each ring component after the coarse or first judgment function, its mean and standard deviation are determined based upon the below equations:

$$\text{mean}(\text{row}, col) = \frac{1}{Nframes} \sum_{frame=0}^{Nframes} Ring'_{row}(\text{frame}, col)$$

$$\sigma^2(\text{row}, col) = \frac{1}{Nframes-1} \sum_{frame=0}^{Nframes} (Ring'_{row}(\text{frame}, col) - \text{mean}(\text{row}, col))^2$$

Where $Ring'_{row}$ is the output from the first ring judgment function as described with respect to the step S400. Nframes is a predetermined number of frames in the patient data set.

Figure 7:
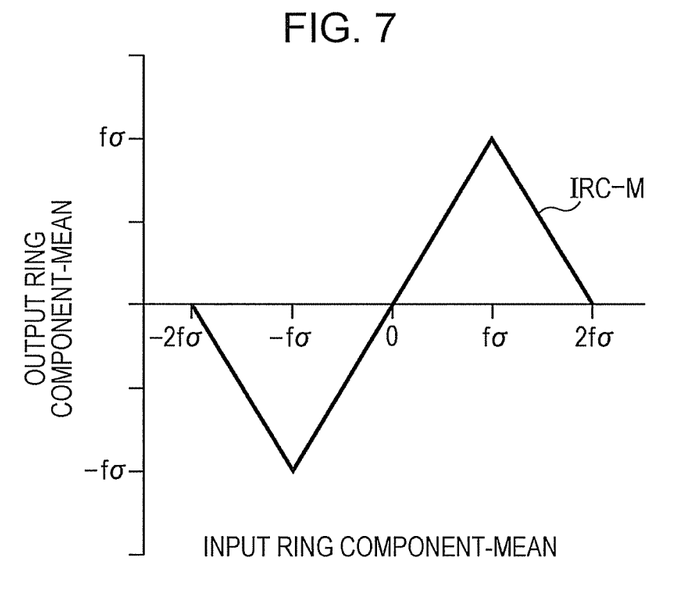
FIG. 7 illustrates one exemplary second ring judgment function IRC-M.

In the step S600, the second judgment function according to the current invention is to further prevent unintended side-effects from the correction by applying fuzzy logic to the ring component candidates from previously determined ring components after the step S300. For example, the input to the second ring judgment includes the ring component candidates after the first ring judgment, fraction of standard deviation to use as a threshold, mean of the ring component and standard deviation of the ring component while the output is the fully corrected ring components of the data after the second ring judgment. FIG. 7 illustrates one exemplary second judgment function IRC-M, and the thresholds are set by fraction of standard deviation to use as a threshold, standard deviation of the ring component and ring component offset by the mean.

The corrected reconstruction data is finally generated in the step S700 as illustrated in one exemplary embodiment of the current invention before the step S800 performs reconstruction on the corrected data. In effect, the step S700 subtracts the ring components as determined by the second ring judgment of the step S600 from the projection data or the output of the predetermined preprocessing. That is, the input to the step S700 includes the true ring components as determined after the second ring judgment and the output of preprocessing while the output of the step S700 is the truly corrected projection data to be used for reconstruction.

Figure 8:
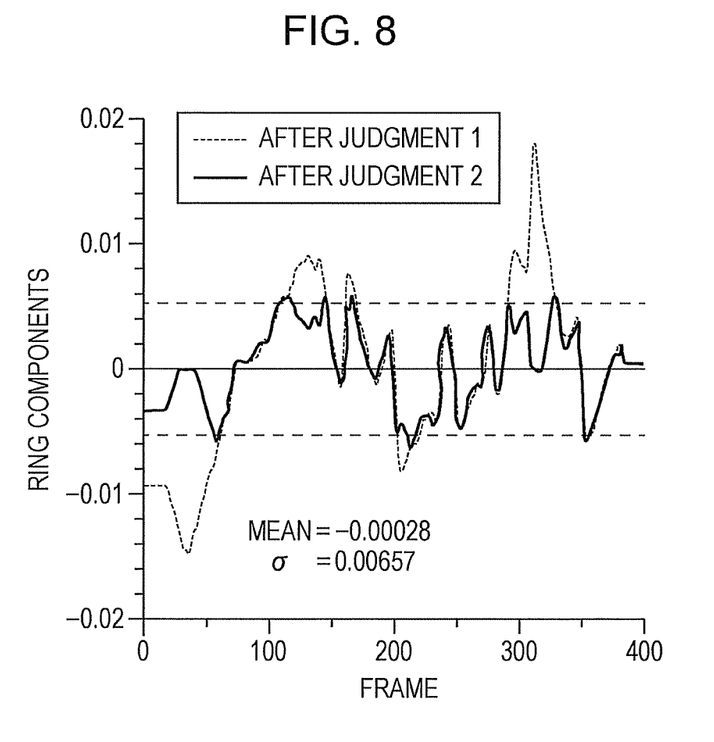
FIG. 8 illustrates the effect of the second ring judgment function in relation to the results after the first ring judgment function in a graph format.

FIG. 8 illustrates the effect of the second ring judgment function in relation to the results after the first ring judgment function in a graph format. After the first ring judgment function, the results of the ring components are shown in the dotted lines. The mean of the ring components is indicated by the solid horizontal line at near 0 on the Y axis while a fraction of the standard deviation, $\pm f \times \sigma$ is indicated by the dashed horizontal lines. For this example and all evaluations, $f=0.8$. Some of these ring components after the first ring judgment function are still above the standard deviation of the ring components. After applying the second ring judgment function such as shown in FIG. 7, the results of the ring components are shown in the solid lines, and the results are all within the prescribed standard deviation according to the current invention. In this embodiment, the mean is subtracted from the ring components before applying the second ring judgment and then added back in. Also, a small value is added to that represents the minimum expected ring amplitude.

Figure 9A:
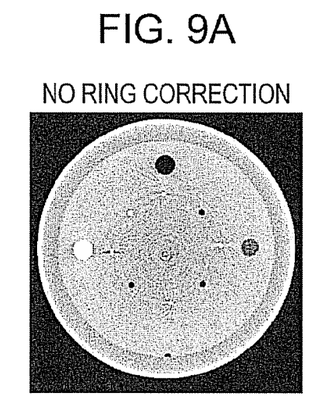
FIGS. 9A, 9B and 9C illustrate a first comparison example among an image with no ring correction, an image with a prior art correction and an image after the exemplary process of sRFC for substantially reducing the ring artifacts according to the current invention.

Now referring to FIG. 9, a comparison is provided for the exemplary process of sRFC for substantially reducing the ring artifacts according to the current invention. FIG. 9A illustrates an image of predetermined functional data using the Catphan with no ring artifact correction. As seen in its center region, multiple concentric rings are visually identified in the image of FIG. 9A.

Figure 9B:
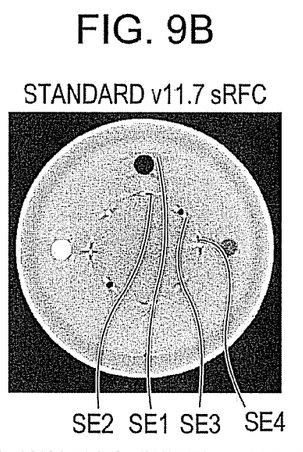

FIG. 9B illustrates a corresponding image of the predetermined functional data with some prior art ring artifact correction. As seen in its center region, multiple concentric rings are no longer noticeable in the image of FIG. 9B. On the other hand, the prior art ring artifact correction introduces multiple side effects SE1 through SE4 in the reconstructed image in FIG. 9B. These newly introduced side effects degrade the clinical significance of the corrected image even though the original ring artifacts may be subsided.

Figure 9C:
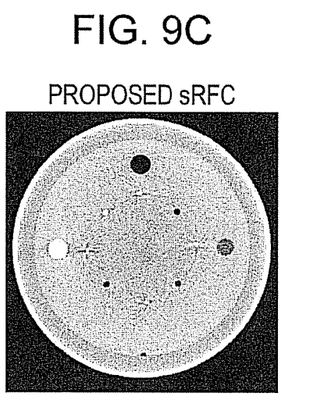

FIG. 9C illustrates a corresponding image of the predetermined functional data with the above discussed exemplary ring artifact correction according to the current invention. That is, sRFC including an additional ring judgment function according to the current invention is performed on the data that has been already corrected at least by a predetermined prior art correction method. As seen in its center region, multiple concentric rings in the original data stay unnoticeable in the image of FIG. 9C. At the same time, the side effects SE1 through SE4 of FIG. 9B are also substantially reduced.

Figure 10A:
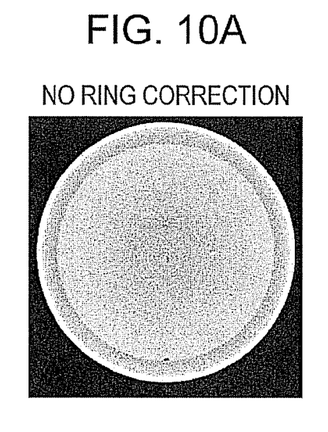
FIGS. 10A, 10B and 10C illustrate a second comparison example among an image with no ring correction, an image with a prior art correction and an image after the exemplary process of sRFC for substantially reducing the ring artifacts according to the current invention.

Now referring to FIG. 10, a comparison is provided for the exemplary process of sRFC for substantially reducing the ring artifacts according to the current invention. FIG. 10A illustrates an image of predetermined functional data using the Catphan with no ring artifact correction. As seen particularly in its center region, multiple concentric rings are visually identified in the image of FIG. 10A.

Figure 10B:
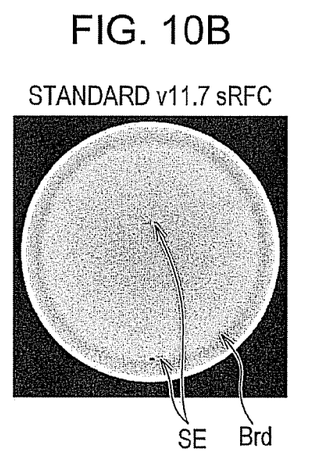

FIG. 10B illustrates a corresponding image of the predetermined functional data with some prior art ring artifact correction. As seen in throughout the regions, multiple concentric rings are no longer noticeable in the image of FIG. 10B. On the other hand, the prior art ring artifact correction introduces new side effects SE in the reconstructed image in FIG. 10B. Furthermore, boundary Brd between inner and outer of the Catphan has been blurred in FIG. 10B. These newly introduced side effects degrade the clinical significance of the corrected image even though the original ring artifacts may be subsided.

Figure 10C:
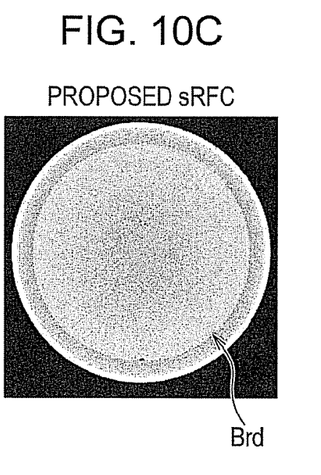

FIG. 10C illustrates a corresponding image of the predetermined functional data with the above discussed exemplary ring artifact correction according to the current invention. That is, sRFC including an additional ring judgment function according to the current invention is performed on the data that has been already corrected at least by a predetermined prior art correction method. As seen throughout the regions, multiple concentric rings in the original data stay unnoticeable in the image of FIG. 10C. At the same time, the side effects of FIG. 10B are also substantially reduced. In addition, the blurred boundary Brd between inner and outer of the Catphan in FIG. 10B has gained sharpness in the image of FIG. 10C.

Figure 11A:
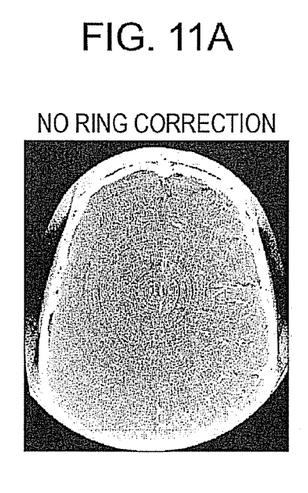
FIGS. 11A, 11B and 11C illustrate a third comparison example among an image with no ring correction, an image with a prior art correction and an image after the exemplary process of sRFC for substantially reducing the ring artifacts according to the current invention.

Now referring to FIG. 11, a comparison is provided for the exemplary process of sRFC for substantially reducing the ring artifacts according to the current invention. FIG. 11A illustrates an image of neural tissue data with no ring artifact correction. As seen particularly in its center region, multiple concentric rings are visually identified in the image of FIG. 11A.

Figure 11B:
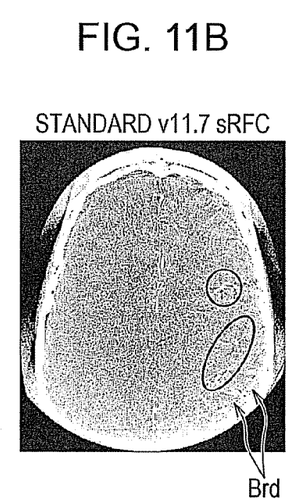

FIG. 11B illustrates a corresponding image of the predetermined functional data with some prior art ring artifact correction. Although the multiple concentric rings are no longer noticeable in the image of FIG. 11B, the prior art ring artifact correction introduces new side effects as marked by an oval and a circle in the reconstructed image in FIG. 11B. Furthermore, boundary Brd has been blurred in FIG. 11B. These newly introduced side effects degrade the clinical significance of the corrected image even though the original ring artifacts may be subsided.

Figure 11C:
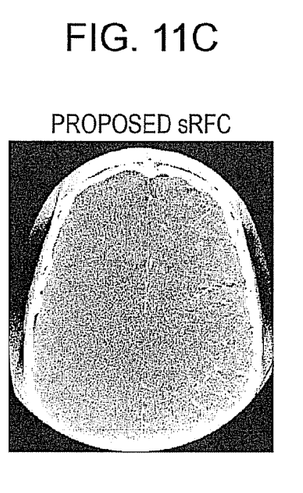

FIG. 11C illustrates a corresponding image of the predetermined functional data with the above discussed exemplary ring artifact correction according to the current invention. That is, sRFC including an additional ring judgment function according to the current invention is performed on the data that has been already corrected at least by a predetermined prior art correction method. As seen throughout the regions, multiple concentric rings in the original data stay unnoticeable in the image of FIG. 11C. At the same time, the side effects of FIG. 11B are also substantially reduced. In addition, the blurred boundary Brd in FIG. 11B has gained sharpness in the image of FIG. 11C.

In the above description of the current invention, although the equations may be simplified for clarity, one of ordinary skill in the art should be able to implement the method based upon disclosures as provided in the current application and or those as explicitly incorporated in the current application for certain aspects. Furthermore, the current invention as exemplified in the above embodiments and processes are merely illustrative and should not be considered to be limiting the current invention. In this regard, it is to be understood, that even though numerous characteristics and advantages of the present invention have been set forth in the foregoing description, together with details of the structure and function of the invention, the disclosure is illustrative only, and that although changes may be made in detail, especially in matters of shape, size and arrangement of parts, as well as implementation in software, hardware, or a combination of both, the changes are within the principles of the invention to the full extent indicated by the broad general meaning of the terms in which the appended claims are expressed.

What is claimed is:

1. A method of substantially reducing ring artifacts in CT images, comprising the steps of:
   a) generating attenuation data from detected intensity signals that have been detected at a data acquisition circuit after being attenuated through an object;
   b) identifying ring-causing components in the attenuation data using a predetermined high-pass filter at a ring reduction device;
   c) preventing unintended side-effects from said step b) by applying a predetermined first judgment function including fuzzy logic to the identified ring-causing components at the ring reduction device;
   d) further correcting the identified ring-causing components using a predetermined second judgment function at the ring reduction device to generate corrected ring-causing components, the second judgment function depending upon a mean value and a standard deviation value of the ring-causing components; and
   e) subtracting the corrected ring-causing components from the attenuation data at the ring reduction device.

2. The method of substantially reducing ring artifacts in CT images according to claim 1, further comprising an additional step of repeating said steps a) through e) for every element of detector elements.

3. The method of substantially reducing ring artifacts in CT images according to claim 1, further comprising an additional step of generating attenuation log data from the attenuation data.

4. The method of substantially reducing ring artifacts in CT images according to claim 1, wherein the second judgment function has a threshold based upon a predetermined percentage of the standard deviation value.

5. The method of substantially reducing ring artifacts in CT images according to claim 4, wherein the second judgment function has candidates of the corrected ring causing components after the predetermined first judgment function, a fraction of standard deviation to use the threshold, the mean value of the ring-causing components and the standard deviation of the ring-causing component, to generate the corrected ring-causing components.

6. The method of substantially reducing ring artifacts in CT images according to claim 1, wherein said identifying step further comprises a combination of additional steps of:
   sorting pseudo-sinograms from the attenuation data; and
   running average to effectively smooth the pseudo-sinograms.

7. A system for substantially reducing ring artifacts in CT images, comprising:
   a data acquisition circuit configured to generate attenuation data from detected intensity signals that have been attenuated through an object; and
   a ring reduction device connected to said data acquisition circuit configured to identify ring-causing components in the attenuation data using a predetermined high-pass filter, said ring reduction device preventing unintended side-effects in the identified ring-causing components by applying a predetermined first judgment function including fuzzy logic to the identified ring-causing components, said ring reduction device further correcting the identified ring-causing components using a predetermined second judgment function to generate corrected ring-causing components, the second judgment function depending upon a mean value and a standard deviation value of the ring-causing components, said ring reduction device subtracting the corrected ring-causing components from the attenuation data.

8. The system for substantially reducing ring artifacts in CT images according to claim 7, wherein said ring reduction device repeatedly identifies ring-causing components and correct the identified ring-causing components for every element of detector elements.

9. The system for substantially reducing ring artifacts in CT images according to claim 7, wherein said data acquisition unit generates attenuation log data from the attenuation data.

10. The system for substantially reducing ring artifacts in CT images according to claim 7, wherein the second judgment function has a threshold based upon a predetermined percentage of the standard deviation value.

11. The system for substantially reducing ring artifacts in CT images according to claim 10, wherein the second judgment function has candidates of the corrected ring causing components after the predetermined first judgment function, a fraction of standard deviation to use the threshold, the mean value of the ring-causing components and the standard deviation of the ring-causing component, to generate the corrected ring-causing components.

12. The system for substantially reducing ring artifacts in CT images according to claim 7, wherein said ring reduction device additionally performs a combination of additional tasks of sorting pseudo-sinograms from the attenuation data, and srunning average to effectively smooth the pseudo-sinograms.

* * * * *